United States Patent
Mitchell

(10) Patent No.: US 12,290,765 B2
(45) Date of Patent: *May 6, 2025

(54) MATERIALS AND METHODS FOR PROCESSING BLOOD SAMPLES

(71) Applicant: Natera, Inc., San Carlos, CA (US)

(72) Inventor: Aoy Tomita Mitchell, Elm Grove, WI (US)

(73) Assignee: Natera, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/582,572

(22) Filed: Feb. 20, 2024

(65) Prior Publication Data

US 2024/0350945 A1   Oct. 24, 2024

Related U.S. Application Data

(63) Continuation of application No. 16/839,319, filed on Apr. 3, 2020, now Pat. No. 11,931,674.

(60) Provisional application No. 62/829,320, filed on Apr. 4, 2019.

(51) Int. Cl.
*B01D 21/26* (2006.01)
*B01L 3/00* (2006.01)
*B04B 5/04* (2006.01)

(52) U.S. Cl.
CPC .......... *B01D 21/262* (2013.01); *B01L 3/5082* (2013.01); *B04B 5/0414* (2013.01)

(58) Field of Classification Search
CPC ..... B01D 21/262; B01D 21/26; B01L 3/5082; B01L 2200/16; B01L 3/50215; B01L 3/5021; B04B 5/0414; A01N 1/0215; A01N 1/0263; A61B 5/15003; A61B 5/150755; A61B 5/154

See application file for complete search history.

(56) References Cited

U.S. PATENT DOCUMENTS

| | | | |
|---|---|---|---|
| 5,258,423 A * | 11/1993 | Crabb | A61L 2/0035 523/136 |
| 11,931,674 B2 * | 3/2024 | Tomita Mitchell | A61B 5/15003 |
| 2007/0207186 A1 * | 9/2007 | Scanlon | A61F 2/91 623/1.42 |
| 2010/0167271 A1 * | 7/2010 | Ryan | G01N 33/56972 435/5 |
| 2011/0111410 A1 * | 5/2011 | Ryan | C12Q 1/6806 435/325 |
| 2014/0227687 A1 * | 8/2014 | Horlitz | C12Q 1/6806 435/6.1 |
| 2014/0274740 A1 * | 9/2014 | Srinivasan | C12Q 1/6809 435/287.2 |
| 2017/0354362 A1 * | 12/2017 | Xu | A61B 5/150251 |
| 2019/0144919 A1 * | 5/2019 | Jackson | A61J 1/05 435/6.1 |
| 2019/0201848 A1 * | 7/2019 | Rao | B01D 63/025 |

FOREIGN PATENT DOCUMENTS

DE   202014010872 U1 *   2/2017

OTHER PUBLICATIONS

English translation of Patent Publication De 202014010872U1, published Oct. 18, 2014. (Year: 2014).*

* cited by examiner

*Primary Examiner* — Joseph W Drodge

(57) ABSTRACT

Provided herein are materials and methods relating to cell-free DNA. In particular, the technology relates to methods and materials for the preparation and handling of blood samples for future use in applications involving cell-free DNA.

14 Claims, No Drawings

MATERIALS AND METHODS FOR PROCESSING BLOOD SAMPLES

CROSS-REFERENCE TO RELATED APPLICATION

This application claims priority to U.S. Provisional Application No. 62/829,320, filed Apr. 4, 2019, which is incorporated herein by reference in its entirety.

FIELD OF INVENTION

Provided herein is technology relating to cell-free DNA. In particular, the technology relates to methods and materials for the preparation and handling of blood samples for future use in applications involving cell-free DNA.

BACKGROUND

Cell-free DNA (cf-DNA) can be isolated from biological samples such as whole blood, plasma, serum, other body fluids (e.g., organ perfusate fluids) and can be analyzed for a variety of purposes, such as transplant monitoring including general assessments of in vivo tissue damage. However, cellular lysis, such as from white blood cells (WBCs) can occur during or after sample collection or processing and result in genomic DNA being released from those cells. This can result in additional DNA from the subject (self) being introduced and can result in the dilution of non-self, such as a transplant donor, fraction. Therefore, what is needed are methods of preparing and handling samples comprising cf-DNA that reduce the risk of cell lysis from WBCs.

SUMMARY

Provided herein are materials and methods for the preparation and handling of blood samples. In some embodiments, disclosed herein are tubes for collecting a blood sample, the tube comprising: an outer wall and a base defining an internal volume for containing the blood sample; a chemical preservative disposed in the internal volume; and a physical separator disposed in the internal volume. Further provided herein are methods for processing a blood sample. The methods comprise providing a first container comprising a blood sample; centrifuging the first container at a first fixed speed to separate the blood sample into at least a plasma component and a blood cell component; isolating the plasma component; and centrifuging the isolated plasma component at a second fixed speed.

Additional embodiments will be apparent to persons skilled in the relevant art based on the teachings contained herein.

DETAILED DESCRIPTION

Described herein are materials and methods for collection and processing of blood samples. In particular embodiments, provided herein are tubes for collection of blood samples. In other embodiments, provided herein are methods for processing blood samples. The materials and methods provided herein may be useful for collection and processing of blood samples suitable for downstream applications involving cell-free DNA.

Definitions

To facilitate an understanding of the present technology, a number of terms and phrases are defined below. Additional definitions are set forth throughout the detailed description.

As used herein, "a" or "an" or "the" can mean one or more than one. For example, "a" widget can mean one widget or a plurality of widgets.

As used herein, the term "sample" and "specimen" are used interchangeably, and in the broadest senses. In one sense, sample is meant to include a blood sample. The blood sample may be a whole blood sample. The terms "whole blood" or "whole blood sample" as used interchangeably herein refer to a blood sample wherein none of the components (e.g. plasma, white blood cells, red bloods cells, or platelets) have been removed. In some instances, the blood sample comprises at least a "plasma component" and a "blood cell component." The term "plasma component" refers to the portion of the blood sample that is devoid of any cells. The term "blood cell component" refers to the portion of the blood sample that contains blood cells. The term "blood cells" as used herein refers to any type of blood cell, including red blood cells, white blood cells, and platelets. The blood sample may be obtained or isolated from any suitable subject.

As used herein, the terms "subject" and "patient" refer to any animal, such as a dog, cat, bird, livestock, and particularly a mammal, preferably a human.

The term "system" as used herein refers to a collection of articles for use for a particular purpose. In some embodiments, the articles comprise instructions for use, as information supplied on e.g., an article, on paper, or on recordable media (e.g., diskette, CD, flash drive, etc.). In some embodiments, instructions direct a user to an online location, e.g., a website.

Embodiments of the Technology

Although the disclosure herein refers to certain illustrated embodiments, it is to be understood that these embodiments are presented by way of example and not by way of limitation.

1. Tubes

In some embodiments, provided herein are tubes for collecting a blood sample. The tubes comprise an outer wall and a base defining an internal volume for containing the blood sample, a chemical preservative disposed in the internal volume, and a physical separator disposed in the internal volume. The outer wall and/or base of the tube may be any suitable material. For example, the outer wall and/or base of the tube may comprise glass. As another example, the outer wall and/or base of the tube may comprise plastic. In some embodiments, the outer wall and base of the tube comprise a suitable plastic material.

The tubes may be any suitable size for collection of the desired volume of blood. For example, the tube may be a suitable size for the collection of about 1 ml to about 20 ml of blood. For example, the tube may be a suitable size for the collection of about 1 ml, about 2 ml, about 3 ml, about 4 ml, about 5 ml, about 6 ml, about 7 ml, about 8 ml, about 9 ml, about 10 ml, about 11 ml, about 12 ml, about 13 ml, about 14 ml, about 15 ml, about 16 ml, about 17 ml, about 18 ml, about 19 ml, or about 20 ml of blood.

a. Chemical Preservative

The tubes comprise a chemical preservative disposed in the internal volume of the tube. The chemical preservative may be any suitable preservative to stabilize blood cells, such as white blood cells. Stabilization of blood cells comprises reducing the risk of cell lysis in the blood sample.

Accordingly, stabilization of blood cells comprises reducing the risk of release of genomic DNA from the blood cells into the sample.

In some embodiments, the chemical preservative may be any one or more of diazolidinyl urea, aldehyde derivatives (e.g. paraformaldehyde, formaldehyde, metaformaldehyde), poloxamers (e.g. P118, P331), polyethylene glycol (PEG) (e.g. PEG 8000), DMSO, glycerol, sucrose, propranolol, dex-propranolol, bilayer lipid membrane stabilizers (e.g. methyacrylate monomers, methyacrylate polymers, bis-dienoyl phosphatidylcholine), TransFix®, and Cyto-chex®. For example, methyacrylate monomers include ethylene glycol dimethacrylate and butyl methacrylate.

b. Physical Separator

The tubes further comprise a physical separator disposed in the internal volume of the tube. The physical separator substantially separates the blood sample into at least a plasma component and a blood cell component. For example, the physical separator may substantially separate the blood sample into at least a plasma component and a blood cell component when the tube is centrifuged. The physical separator may be designed to migrate in the tube during centrifugation such that the physical separator substantially separates the blood sample into at least a plasma component and a blood cell component after the tube has been centrifuged. Separation of the blood sample into at least a plasma component and a blood cell component may be achieved by centrifuging the tube at any suitable speed. For example, the tube may be centrifuged at a speed ranging from about 500×g to about 2000×g. For example, the tube may be centrifuged at about 500×g, about 600×g, about 700×g, about 800×g, about 900×g, about 1000×g, about 1100×g, about 1200×g, about 1300×g, about 1400×g, about 1500×g, about 1600×g, about 1700×g. about 1800×g, about 1900×g, or about 2000×g.

The blood cell component may comprise a red blood cell component and a white blood cell component. Accordingly, the physical separator may substantially separate the blood sample into a plasma component, a white blood cell component, and a red blood cell component. The white blood cell component may include both white blood cells and platelets. A white blood cell component including both white blood cells and platelets is also referred to herein as a "buffy coat".

The physical separator may additionally prevent aspiration of the blood cell component during subsequent isolation of the plasma component from the tube. For example, the physical separator may prevent aspiration of cells in the buffy coat (e.g., white blood cells and/or platelets) during subsequent isolation of the plasma component from the tube.

The physical separator may be any suitable material. For example, the physical separator may be a gel, such as a polyester-based polymer gel. The physical separator may also be referred to herein as a "plug" or a "gel plug".

The tubes described herein may be used in a method for collecting a blood sample, comprising adding the blood sample to a tube as described herein.

2. Sample Processing

In some embodiments, provided herein are methods for processing a blood sample. The methods comprise providing a first container comprising a blood sample. For example, the first container may comprise a whole blood sample. Providing a first container comprising a blood sample may include isolating blood from a subject into the first container (e.g., drawing blood from the subject) or may include obtaining a first container that already contains the blood sample. In some embodiments, the methods for processing a blood sample are performed less than 7 hours after blood has been obtained from the subject. For example, the methods for processing a blood sample may be performed less than 7 hours, less than 6 hours, less than 5 hours, less than 4 hours, less than 3 hours, less than 2 hours, or less than 1 hour after blood has been obtained from the subject.

The methods further comprise centrifuging the first container at a first fixed speed to separate the blood sample into at least a plasma component and a blood cell component. For example, centrifuging the first container at the first fixed speed may separate the blood sample into a plasma component, a white blood cell component, and a red blood cell component. The white blood cell component may include both white blood cells and platelets.

The first fixed speed may be any suitable speed for separation of the blood sample. For example, the first fixed speed may be any speed ranging from about 500×g to about 2000×g. For example, the first fixed speed may be about 500×g, about 600×g, about 700×g, about 800×g, about 900×g, about 1000×g, about 1100×g, about 1200×g, about 1300×g, about 1400×g, about 1500×g, about 1600×g, about 1700×g. about 1800×g, about 1900×g, or about 2000×g.

Centrifugation at the first fixed speed may be performed for any suitable duration of time. For example, centrifugation at the first fixed speed may be performed for 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, or 20 minutes. In some embodiments, centrifugation at the first fixed speed is performed for 10 minutes.

In some embodiments, the white blood cell component may be isolated after centrifuging the first container at the first fixed speed. The isolated white blood cell component may be stored at a suitable temperature. For example, the isolated white blood cell component may be stored at a temperature of −20° C. or colder. For example, the isolated white blood cell component may be stored at a temperature of about −20° C., about −30° C., about −40° C., about −50° C., about −60° C., about −70° C., or about −80° C.

The methods further comprise isolating the plasma component and centrifuging the isolated plasma component at a second fixed speed. After centrifuging at the second fixed speed, the resulting, further purified plasma component is isolated. In some embodiments, this plasma component is isolated and store at a suitable temperature. For example, the isolated plasma component may be stored at a temperature of −20° C. or colder. For example, the isolated plasma component may be stored at a temperature of about −20° C., about −30° C., about −40° C., about −50° C., about −60° C., about −70° C., or about −80° C.

The second fixed speed may be any suitable speed. For example, the second fixed speed may be any speed ranging from about 500×g to about 2000×g. For example, the first fixed speed may be about 500×g, about 600×g, about 700×g, about 800×g, about 900×g, about 1000×g, about 1100×g, about 1200×g, about 1300×g, about 1400×g, about 1500×g, about 1600×g, about 1700×g. about 1800×g, about 1900×g, or about 2000×g.

Centrifugation at the second fixed speed may be performed for any suitable duration of time. For example, centrifugation at the second fixed speed may be performed for 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, or 20 minutes. In some embodiments, centrifugation at the second fixed speed is performed for 10 minutes.

In some embodiments, the first fixed speed and the second fixed speed are different. In other embodiments, the first fixed speed and the second fixed speed may be the same. For example, the first fixed speed and the second fixed speed may each be 1100×g. In other embodiments, the first fixed speed and the second fixed speed may each be 1400×g.

The first container may comprise any suitable tube. In some embodiments, the first container may comprise a tube having an outer wall and a base defining an internal volume for containing the blood sample, a chemical preservative disposed in the internal volume, and a physical separator disposed in the internal volume as described herein. However, the methods for processing a blood sample described herein may also be performed with other suitable first containers. For example, the first container may be a tube comprising a chemical preservative disposed in the internal volume of the tube but lacking a physical separator disposed in the internal volume. Alternatively, the first container may be a tube comprising a physical separator disposed in the internal volume of the tube but lacking a chemical preservative designed to stabilize white blood cells.

3. Applications

The tubes and sample processing methods described herein may be used in a variety of downstream applications. For example, the plasma isolated after the second centrifugation may be used for detection and/or quantification of cell-free DNA. Cell-free DNA from plasma collected in the disclosed tubes or by the described methods can be used for a variety of applications. Suitable applications for cell-free DNA include rare variant analysis such as in non-invasive prenatal testing, liquid biopsy for cancer, and transplant monitoring. Exemplary methods for methods involving analysis of cell-free DNA are provided in U.S. Pat. Nos. 10,385,396, 10,472,680, U.S. Patent Publication No. 20200032340 A1, U.S. Patent Publication No. 20190367972 A1, PCT Publication No. WO2018237075 A1, PCT Publication No. WO2018237081 A1, PCT Publication No. WO2018237078 A1, PCT Publication No. WO2019035995 A1, and PCT Publication No. WO2019118926 A1, each of which are incorporated herein by reference in their entireties.

Cell-free DNA may also be determined by a MOMA assay. Any one of the tubes or methods provided herein can be used in a MOMA assay such as described in PCT Publication No. WO2016176662 A1, PCT Publication No. WO2019217918A1, PCT Publication No. WO2017190104A1, PCT Publication No. WO2017190105A1, PCT Publication No. WO2017190106A1, and PCT Publication No. WO2018085597A1, each of which are incorporated herein by reference in their entireties.

Downstream use of the samples (e.g. the isolated plasma component and/or the isolated white blood cell component) obtained by the methods described herein may occur at the same site that the blood sample was processed (e.g. subjected to the first and second centrifugation steps) or at a different site. Additionally, the blood sample may be isolated from the subject at the same site that the blood sample is processed or at a different site.

For example, the blood sample may isolated from the subject at a first site, such as a hospital or a clinic. The isolated blood may be placed in a suitable container and processed by the methods described herein at the first site. In some embodiments, the isolated blood may be placed in a tube comprising a chemical preservative and a physical separator as described herein. The isolated blood components (i.e. the isolated plasma component and/or isolated white blood cell component) obtained from the sample by the processing methods described herein may be used at the first site for the desired downstream application. Alternatively, the isolated blood components obtained by the processing method may be transported to a second site for downstream use.

If the isolated blood components are to be transported to a second site for downstream use, proper storage and handling of the isolated blood components before and during transportation may prevent unwanted damage prior to downstream use. In some embodiments, the isolated blood components may be stored at the first site at a temperature of −20° C. or colder until the isolated blood components are frozen. For example, the isolated plasma component and/or isolated white blood cell component may be stored at a temperature of about −20° C. to about −80° C. for at least one hour (e.g. at least 1 hour, at least 2 hours, at least 3 hours, at least 4 hours, at least 5 hours, at least 6 hours, at least 7 hours, at least 8 hours, at least 9 hours, at least 10 hours, at least 11 hours, or at least 12 hours). The frozen isolated blood components may then be packaged and shipped to the desired second site. Suitable packaging materials include absorbent pouches, biohazard bags, cold-packs, ice, dry-ice, boxes (e.g. Styrofoam boxes), and the like. For example, the frozen isolated blood components may packaged in a box, such as a Styrofoam box, containing dry-ice such that the samples remain frozen during shipment to the second site. The temperature of the shipping environment may also be monitored. For example, a temperature logger may be placed on box containing the samples (e.g., on a lid of the box) or in the box containing the samples.

4. Kits

It is contemplated that embodiments of the technology are provided in the form of a kit. The kits comprise embodiments of the materials and methods described herein, and instructions for use of the kit. Individual components of the kit are packaged in appropriate containers and packaging (e.g., vials, boxes, blister packs, ampules, jars, bottles, tubes, and the like) and the components are packaged together in an appropriate container (e.g., a box or boxes) for convenient storage, shipping, and/or use by the user of the kit. For example, the kits may comprise one or more tubes for collecting a blood sample as described herein. The kits are appropriate for use in a clinical setting and, in some embodiments, for use in a user's home. The components of a kit, in some embodiments, provide the functionalities of a system for preparing a nucleic acid solution from a sample. In some embodiments, certain components of the system are provided by the user.

EXAMPLES

Example 1

During the development of embodiments of the technology provided herein, it was demonstrated that tubes comprising a physical separator and a chemical preservative demonstrates reduced cell lysis in plasma compared to tubes comprising only a chemical preservative or only a physical separator.

Blood was drawn from four different individuals into 3 different tube types (one with chemical preservative, one without chemical preservative, and one with a physical cell separator). Cell lysis in plasma was lower from tubes that used a cell preservation in comparison with tubes without a cell preservation chemical.

Levels of cell lysis in a cell tube with a chemical preservative a tube with a separator plug, and a tube comprising both a chemical preservative and a physical separator were compared. The combination tube had the least cell lysis.

In a follow-up experiment, the tubes were tested again with samples from 5 different donors. Cell lysis was lowest in the combination tube.

Taken together, these results demonstrate that the combination tube was superior to tubes without preservatives or separation or tubes having only preservatives or separation. The combination tubes offer superior cell-free DNA tubes for analysis for non-invasive applications such as cancer, transplant rejection, and prenatal testing, among other uses.

I claim:

1. A method for quantifying cell-free DNA, the method comprising:
   (a) providing a tube comprising
      an outer wall and a base defining an internal volume for containing a blood sample;
      a chemical preservative disposed in the internal volume, wherein the chemical preservative comprises one or more of metaformaldehyde, paraformaldehyde, poloxamer, glycerol, propranolol, dex-propranolol, methacrylate monomer, methacrylate polymer, or bis-dienoyl phosphatidylcholine;
      a physical separator disposed in the internal volume, wherein the physical separator substantially separates the blood sample into at least a plasma component and a blood cell component when the tube is centrifuged and prevents aspiration of the blood cell component during subsequent isolation of the plasma component from the tube; and
      a blood sample disposed in the tube;
   (b) centrifuging the tube at a first fixed speed to separate the blood sample into at least a plasma component and a blood cell component;
   (c) isolating the plasma component;
   (d) centrifuging the isolated plasma component at a second fixed speed to obtain a purified plasma component, wherein the first fixed speed and the second fixed speed are each independently selected from a speed ranging from 500×g to 2000×g; and
   (e) quantifying cell-free DNA present in the further purified plasma component.

2. The method of claim 1, further comprising isolating the further purified plasma component after step (d).

3. The method of claim 2, further comprising storing the isolated further purified plasma component at a temperature of −20° C. or colder.

4. The method of claim 2, comprising determining an amount of cf-DNA in the further purified isolated plasma component.

5. The method of claim 1, wherein the blood cell component includes a white blood cell component and a red blood cell component.

6. The method of claim 5, further comprising isolating the white blood cell component after step (b).

7. The method of claim 6, wherein the method further comprises storing the isolated white blood cell component at a temperature of −20° C. or colder.

8. The method of claim 1, wherein the first fixed speed and the second fixed speed are the same.

9. The method of claim 8, wherein the first fixed speed and the second fixed speed are each 1100×g.

10. The method of claim 8, wherein the first fixed speed and the second fixed speed are each 1400×g.

11. The method of claim 1, wherein step (e) comprises quantifying cell-free DNA comprising at least one mutation.

12. The method of claim 1, wherein step (e) comprises quantifying cell-free DNA derived from a transplant.

13. The method of claim 1, wherein step (e) comprises quantifying cell-free DNA derived from a cancer.

14. The method of claim 1, wherein step (e) comprises quantifying cell-free DNA derived from a fetus.

* * * * *